(12) United States Patent
Matsuda

(10) Patent No.: US 7,170,601 B2
(45) Date of Patent: Jan. 30, 2007

(54) FLOW CELL, AND PARTICLE MEASUREMENT DEVICE USING THE SAME

(75) Inventor: Tomonobu Matsuda, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 10/528,900

(22) PCT Filed: Sep. 27, 2002

(86) PCT No.: PCT/JP02/10104

§ 371 (c)(1),
(2), (4) Date: Mar. 23, 2005

(87) PCT Pub. No.: WO2004/029589

PCT Pub. Date: Apr. 8, 2004

(65) Prior Publication Data

US 2006/0001874 A1    Jan. 5, 2006

(51) Int. Cl.
*G01N 21/00* (2006.01)
(52) U.S. Cl. ..................... 356/336; 356/337
(58) Field of Classification Search ........ 356/335–343, 356/440, 442, 434, 436; 250/574–575, 222.2, 250/573, 576; 435/6, 7.1, 7.9
See application file for complete search history.

(56) References Cited

U.S. PATENT DOCUMENTS

| 3,710,933 | A | * | 1/1973 | Fulwyler et al. | 209/3.1 |
| 4,276,475 | A | * | 6/1981 | Nelson | 250/373 |
| 4,906,094 | A | * | 3/1990 | Ashida | 356/336 |
| 5,371,585 | A | * | 12/1994 | Morgan et al. | 356/246 |
| 5,506,673 | A | * | 4/1996 | Kosaka et al. | 356/72 |
| 5,601,983 | A | * | 2/1997 | Takayama et al. | 435/6 |
| 5,633,503 | A | * | 5/1997 | Kosaka | 250/458.1 |
| 6,118,536 | A | * | 9/2000 | Sakamoto et al. | 356/364 |
| 6,184,983 | B1 | * | 2/2001 | Yamaguchi et al. | 356/335 |
| 6,465,802 | B1 | * | 10/2002 | Matsuda | 250/574 |

FOREIGN PATENT DOCUMENTS

| JP | 11-211650 | 8/1999 |
| JP | 11-211651 | 8/1999 |

* cited by examiner

Primary Examiner—Gregory J. Toatley, Jr.
Assistant Examiner—Sang H. Nguyen
(74) Attorney, Agent, or Firm—Carrier, Blackman & Associates, P.C.; Joseph P. Carrier; William D. Blackman

(57) ABSTRACT

A flow cell is provided which can detect scattered light more efficiently by fully utilizing the condensing angle of a condenser lens. A particle monitoring area M is formed within the flow cell by irradiating the area with laser light La, and scattered light Ls generated by particles contained in sample fluid passing through the particle monitoring area M is condensed by the condenser lens L so as to obtain information including diameter of the particles, and inner walls of the flow cell are shaped or arranged such that the scattered light Ls is condensed in a state where the condensing angle θ of the condenser lens L is fully utilized.

20 Claims, 4 Drawing Sheets

FIG. 6 (a) Prior Art
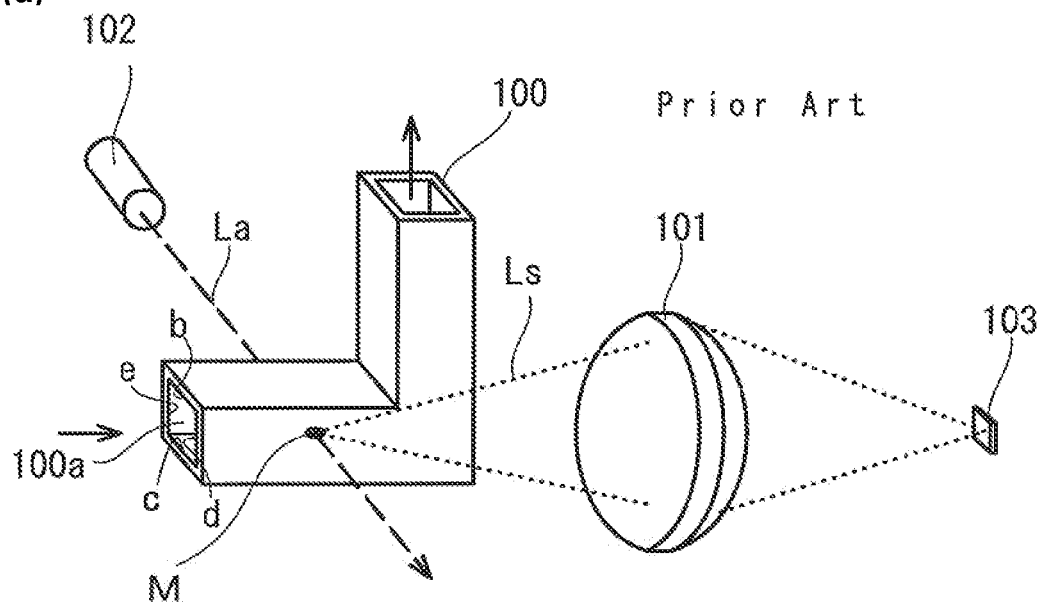
FIG. 6 (b) Prior Art
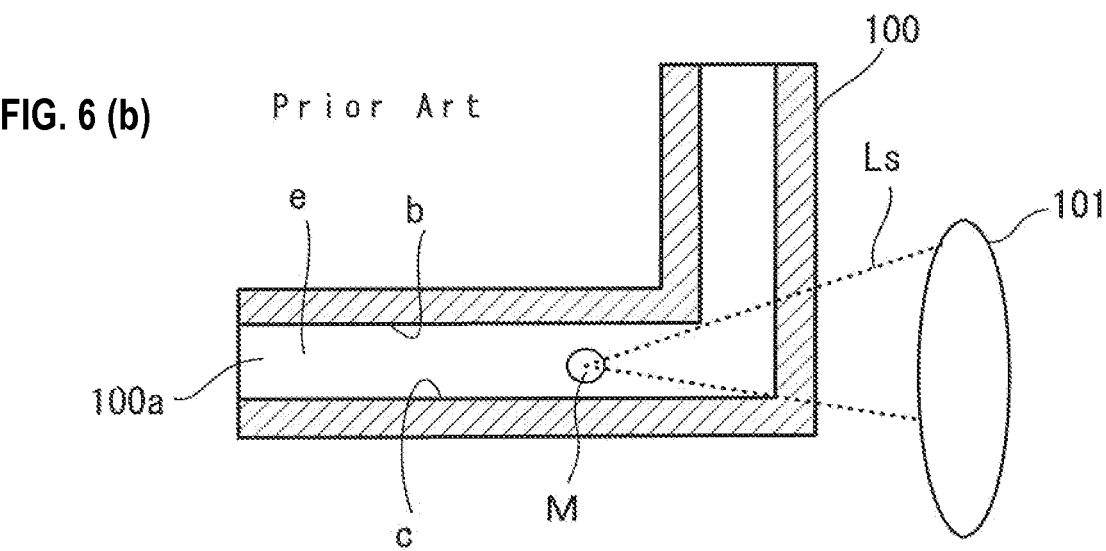
FIG. 6 (c) Prior Art
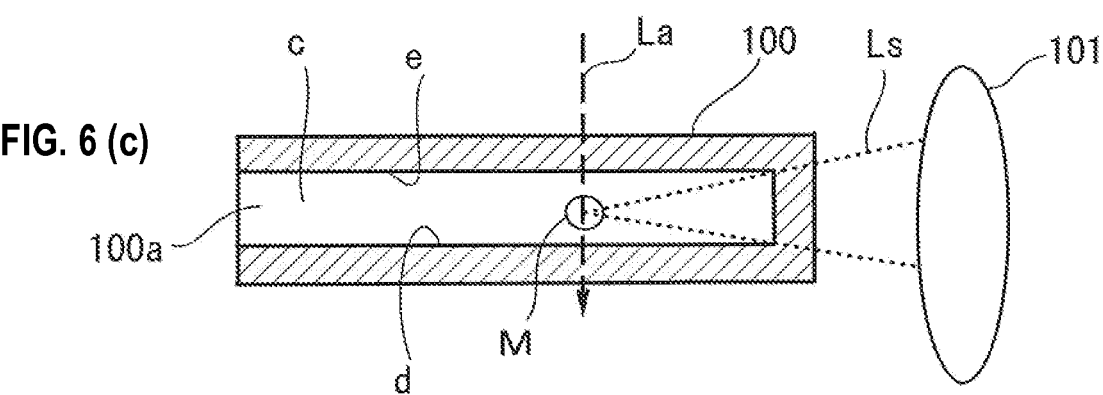

FLOW CELL, AND PARTICLE MEASUREMENT DEVICE USING THE SAME

TECHNICAL FIELD

The present invention relates to a flow cell for flowing sample fluid therethrough to detect light scattered by particles contained in the sample fluid when irradiated with light so as to obtain information such as a particle diameter, and also relates to a particle measuring apparatus using the flow cell.

BACKGROUND ART

A flow cell 100 used for a conventional particle measuring apparatus as shown in FIG. 6(a) is made of a transparent member, and provided with a linear passage 100a having a predetermined length, the cross-sectional shape of which is rectangular. Also, the shape of the flow cell is an L-shaped tube as a whole. The central axis of the linear passage 100a substantially corresponds with the axis of receiving scattered light Ls by a condenser lens system 101 (See Japanese Patent Application Publication No. 11-211650). Incidentally, reference number 102 refers to a laser light source, and reference number 103 refers to a photoelectric transducer element.

In the flow cell 100 used for a conventional particle measuring apparatus, inner walls b, c, d, and e disadvantageously limit the path of light scattered Ls by particles passing through a particle monitoring area M, and the condensing angle of the condenser lens system 101 cannot be fully utilized.

Contrary to the conventional apparatus, if the level of detecting scattered light, and hence the accuracy of detecting particles, is to be improved, it is necessary to fully utilize the condensing angle of the condenser lens system 101.

The present invention was made to solve the above-mentioned drawbacks, and the object of the present invention is to provide a flow cell which can detect scattered light more efficiently by fully utilizing the condensing angle of a condenser means, and also a particle measuring apparatus using the flow cell.

SUMMARY OF THE INVENTION

For solving the above-mentioned drawbacks, according to an aspect of the present invention, there is provided a flow cell in which a particle monitoring area is formed within the flow cell by irradiating the area with light, and light scattered by particles contained in sample fluid passing through the particle monitoring area is condensed by a condenser so as to obtain information including diameter of the particles, wherein inner walls of the flow cell are arranged such that the light scattered by particles is condensed in a state where the condensing angle of the condenser is fully utilized.

According to another aspect of the present invention, there is provided a particle measuring apparatus comprising the above-mentioned flow cell, a light source for irradiating sample fluid flowing through the flow cell to form the particle monitoring area, and an optical detecting and processing means for detecting and processing light scattered or diffracted by particles in the particle monitoring area.

BRIEF DESCRIPTION OF THE DRAWINGS

FIG. 6(a) shows a schematic structure of a conventional particle measuring apparatus, FIG. 6(b) is a longitudinal sectional view of a conventional flow cell, and FIG. 6(c) is a cross-sectional view of the conventional flow cell.

DETAILED DESCRIPTION OF THE INVENTION

Preferred embodiments of the present invention will now be described with reference to the accompanying drawings.

Figure 1:
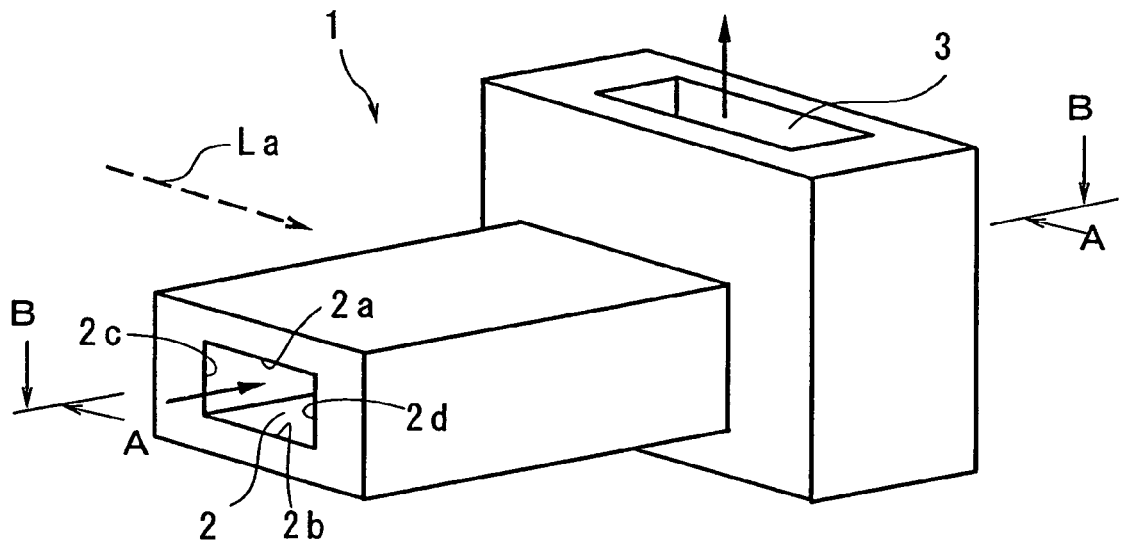
FIG. 1 is a perspective view of the first embodiment of a flow cell according to the present invention.
Figure 2A:
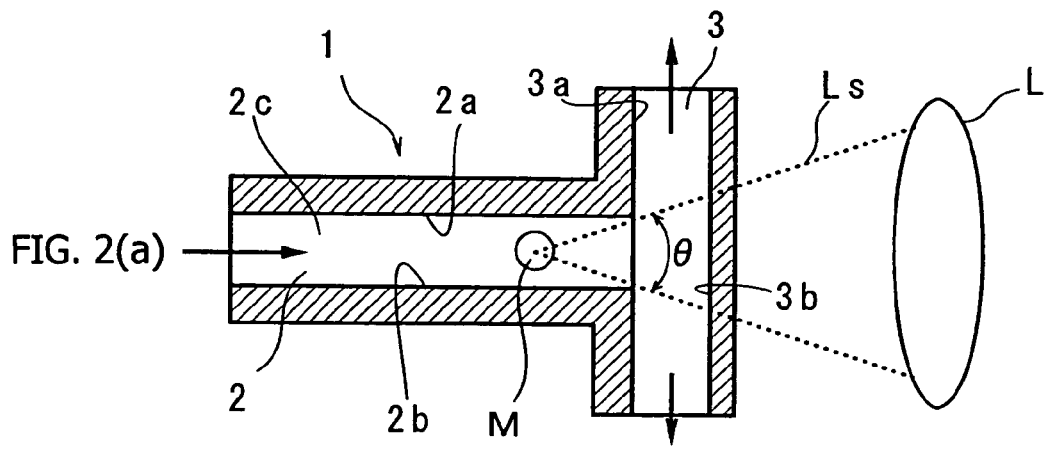
FIG. 2(a) is a sectional view seen from direction A—A of FIG. 1
Figure 2B:
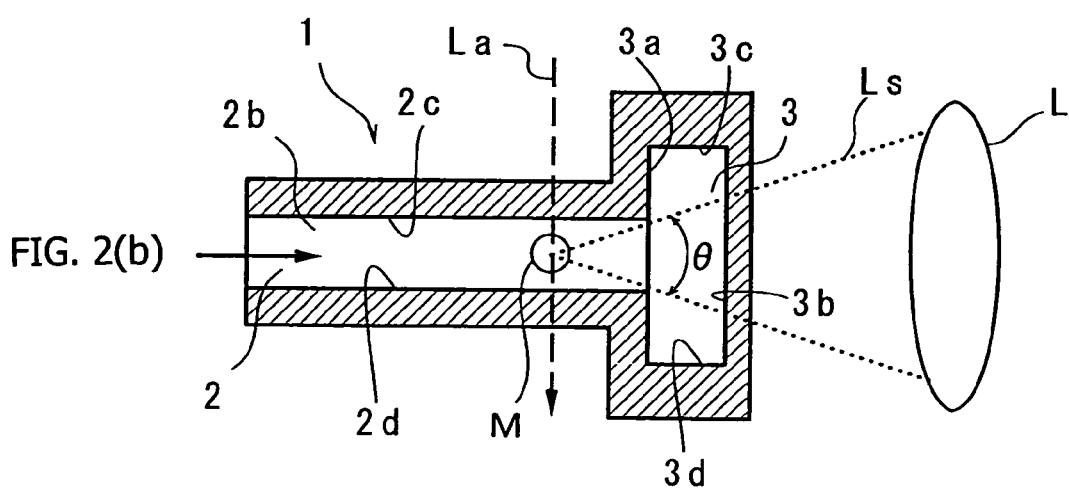
FIG. 2(b) is a sectional view seen from direction B—B of FIG. 1.
Figure 3:
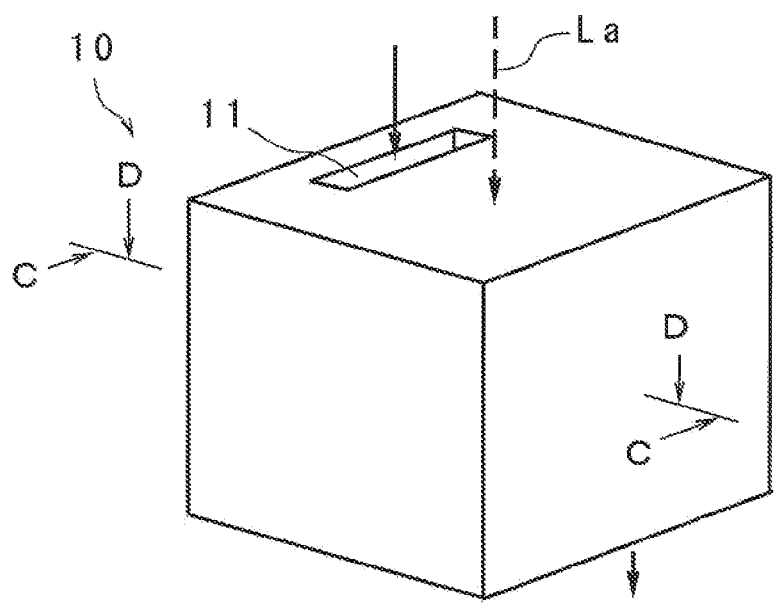
FIG. 3 is a perspective view of the second embodiment of a flow cell according to the present invention.
Figure 4:
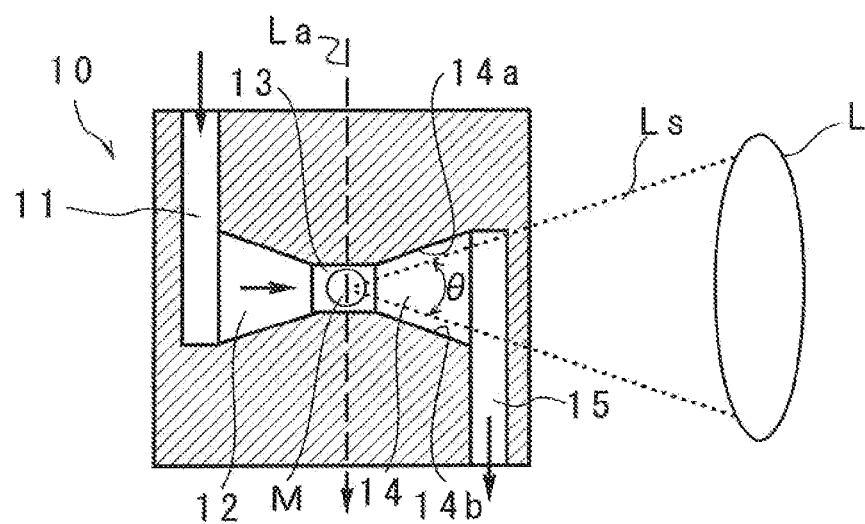
FIG. 4(a) is a sectional view seen from direction C—C of FIG. 3 and FIG. 4(b); is a modification thereof including two condenser lenses each placed on opposite sides of the particle measuring apparatus, is a sectional view seen from direction D—D of FIG. 3.
Figure 4:
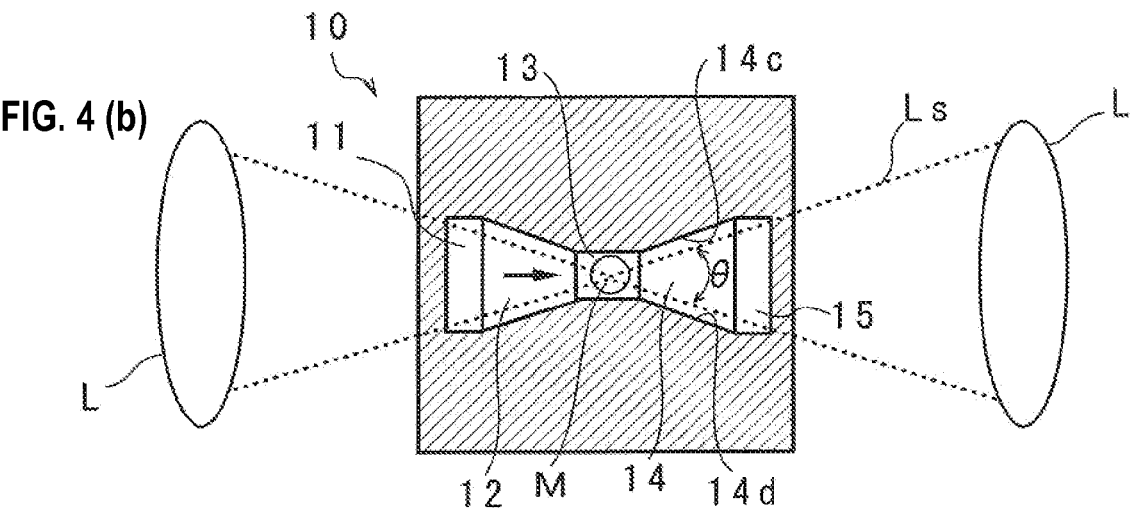
Figure 5:
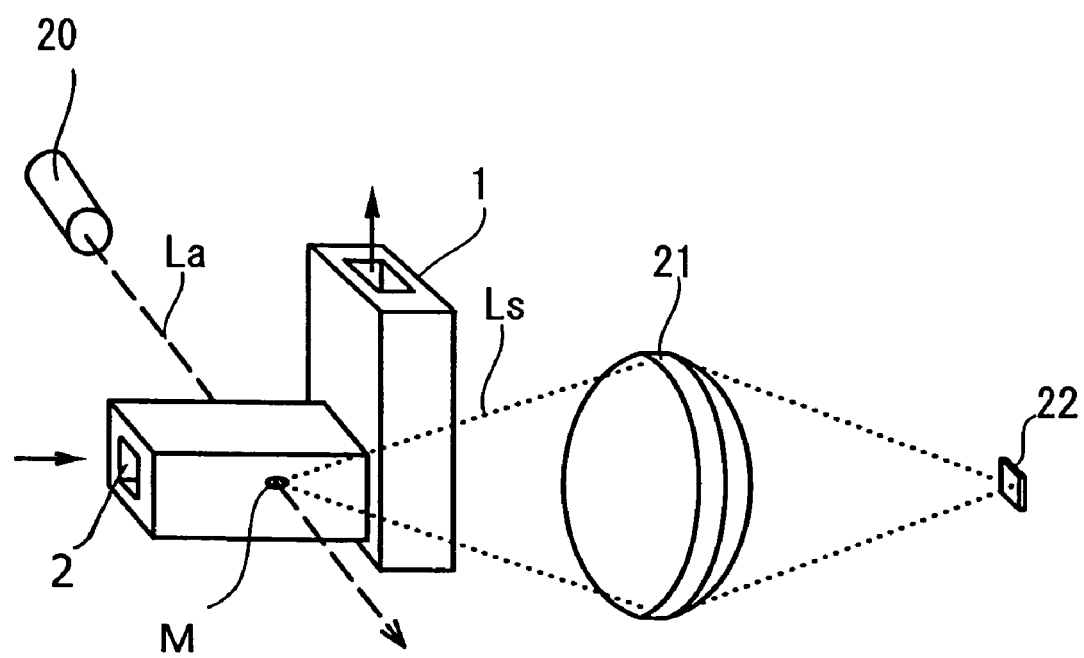
FIG. 5 shows a schematic structure of a particle measuring apparatus according to the present invention.

FIG. 1 is a perspective view of the first embodiment of a flow cell according to the present invention, FIG. 2(a) is a sectional view seen from direction A—A of FIG. 1 and FIG. 2(b) is a sectional view seen from direction B—B of FIG. 1, FIG. 3 is a perspective view of the second embodiment of a flow cell according to the present invention, FIG. 4(a) is a sectional view seen from direction C—C of FIG. 3 and FIG. 4(b) is a sectional view seen from direction D—D of FIG. 3, and FIG. 5 shows a schematic structure of a particle measuring apparatus according to the present invention.

As shown in FIGS. 1–2(b), the flow cell 1 of the first embodiment is made of a transparent member, and provided with a passage 2 (a first passage) for flowing sample fluid therethrough in a direction of the arrow so as to form a particle monitoring area M with respect to laser light La, and another passage 3 (a second passage) having two exits at opposite ends which is perpendicular to the passage 2 and located between the passage 2 and a condenser lens L. As it will be understood from FIGS. 1–2(b), the second passage extends continuously from the first passage; and a width of the second passage is greater than a width of the first passage.

The passage 2 is comprised of four inner walls 2a, 2b, 2c, and 2d, and the cross section is made rectangular. The passage 3 is also comprised of four inner walls 3a, 3b, 3c, and 3d, and the cross section is made rectangular.

The particle monitoring area M is formed in a position where the four inner walls 2a, 2b, 2c, and 2d of the passage 2 do not hinder scattered light Ls from entering the outmost peripheral portion of the condenser lens L for condensing the scattered light Ls, so as to fully utilize the condensing angle of the condenser lens L.

As shown in FIG. 2(a), both ends of the passage 3 are opened. By comparison of FIG. 2(a) with the conventional flow cell 100 in FIG. 6(b), it will be understood that a portion of the inner wall c in the linear passage 100a shown in FIG. 6(b), which limits the path of scattered light Ls, is effectively removed or eliminated in the flow cell 1. Consequently, the scattered light Ls is not hindered or impeded from entering the outmost periphery portion of the condenser lens L.

In addition, as shown in FIG. 2(b), the distance between the inner wall 3c and the inner wall 3d is arranged to be greater than the distance between the inner wall 2c and the inner wall 2d so as not to hinder scattered light Ls from entering the outmost peripheral portion of the condenser lens L by the inner walls 3c and 3d. Conversely, in the conventional flow cell 100 shown in FIGS. 6 and 6(c), the distance between walls d and e is comparable to that between walls b and c such that the walls d and e hinder the scattered light Ls from entering the outmost peripheral portion of the condenser lens L.

In the above-mentioned flow cell 1 of the first embodiment, scattered light Ls generated by particles contained in sample fluid passing through the particle monitoring area M can be condensed in a state where the condensing angle θ of the condenser lens L is fully utilized.

Incidentally, in the first embodiment, both ends of the passage 3 are opened so as to form exits. However, it is also possible to open only one end of the passage 3 and close the other end. In this case, the inner wall for closing the other end must be arranged so as not to hinder scattered light Ls from entering the outmost peripheral portion of the condenser lens L.

Next, as shown in FIGS. 3 and 4, the flow cell 10 of the second embodiment is made of a transparent member, and provided with a passage 11 having a cross section of a rectangular shape, a passage 12 of a pyramidal shape, a passage 13 having a cross section of a rectangular shape, a passage 14 having a pyramidal shape, and a passage 15 having a cross section of a rectangular shape. The particle monitoring area M is formed within the passage 13 by irradiating sample fluid flowing through the passage 13 in a direction of the arrow with laser light La.

The passage 13 is arranged to have a cross-sectional area and a length such that a particle monitoring area M having a desired size can be formed. The passages 11 and 15, and the passages 12 and 14 are positioned so as to be symmetrical with respect to the center of the passage 13, respectively.

In addition, as shown in FIGS. 4(a) and 4(b), four inner walls 14a, 14b, 14c, and 14d of the passage 14 are formed so as not to hinder or impede scattered light Ls from entering the outmost peripheral portion of the condenser lens L. With this, the condensing angle θ of the condenser lens L for condensing the scattered light Ls can be fully utilized.

In the above-mentioned flow cell 10 of the second embodiment, scattered light Ls generated by particles contained in sample fluid passing through the particle monitoring area M can be condensed in a state where the condensing angle θ of the condenser lens L is fully utilized.

Incidentally, in the second embodiment, the passages 12 and 14 are made in a pyramidal shape. However, a conical shape is also possible. Also, another condenser lens L may be provided in the opposite position with respect to the flow cell 10, on the opposite side of the flow cell from the condensing lens L in FIGS. 4(a), 4(b), so as to double the scattered light detecting capability. In other words, with two condenser lenses L, L each placed on opposite sides of the flow cell 10, as shown in FIG. 4(b), scattered light detecting capability of the particle measuring apparatus can be doubled.

It is not essential that all portions of the flow cells 1 and 10 are made of a transparent material. It is possible to form the portions where light does not pass with a non-transparent material. In addition, it is not essential that the flow cells 1 and 10 are formed as a unitary member. The same function can be achieved by combing a plurality of members.

Next, as shown in FIG. 5, the particle measuring apparatus according to the present invention is comprised of the flow cell 1, a laser light source 20, a condenser lens system 21 including the condenser lens L, and a photoelectric transducer element 22. The flow cell 10 shown in FIG. 3 can be used instead of the flow cell 1 in such apparatus.

The particle monitoring area M is formed by irradiating a predetermined area of the passage 2 of the flow cell 1 with laser light La from the laser light source 20. The optical axis of the laser light Ls is substantially perpendicular to the central axis of the passage 2 within the flow cell 1.

The condenser lens system 21 has an optical axis which corresponds to the central axis of the passage 2, and condenses scattered light Ls generated by particles which has been irradiated with the laser light La in the particle monitoring area M. Incidentally, the condenser lens system 21 does not always need to be positioned on the central axis of the passage 2.

The photoelectric transducer element 22 is provided on the optical axis of the condenser lens system 21, and receives the scattered light Ls which has been condensed by the condenser lens system 21 so as to transduce the scattered light Ls into voltage, which varies depending on the intensity of the scattered light Ls. The condenser lens system 21 and subsequent elements are referred to as an optical detecting and processing means.

In operation, a predetermined area of the passage 2 is irradiated with laser light La which has been emitted from the laser light source 20 so as to form a particle monitoring area M. When particles contained in sample fluid pass through the particle monitoring area M, the particles are irradiated with the laser light La and scattered light Ls is generated.

The scattered light Ls is condensed by the condenser lens system 21 toward the photoelectric transducer element 22 in a state where the condensing angle of the condenser lens system 21 is fully utilized due to the shape of the passages 2 and 3. Next, the scattered light Ls which has been condensed toward the photoelectric transducer element 22 is transduced into voltage which varies depending on the intensity of the scattered light Ls.

Since the shape of the passages 2 and 3 is arranged such that the condenser lens system 21 can condense the scattered light Ls toward the photoelectric transducer element 22 in a state where the condensing angle θ is fully utilized, the detection level can be improved.

INDUSTRIAL APPLICABILITY

As mentioned above, according to an aspect of the present invention, scattered light generated by particles contained in sample fluid passing through the particle monitoring area can be condensed in a state where the condensing angle of the condenser means is fully utilized.

According to another aspect of the present invention, since the shape of the passage of the flow cell is arranged such that optical detecting and processing means can condense the scattered light in a state where the condensing angle is fully utilized, the detection level can be improved.

Although there have been disclosed what are the present embodiments of the invention, it will be understood that variations and modifications may be made thereto without departing from the spirit of scope of the invention as indicated by the appended claims.

The invention claimed is:

1. A particle measuring apparatus comprising:
    a flow cell having a first passage and a second passage extending continuously from the first passage;
    a particle monitoring area formed in the first passage by irradiating the flow cell with light; and
    a condenser which condenses light scattered by particles contained in sample fluid passing through the particle monitoring area so as to obtain information including diameter of the particles,
    wherein a central axis of the first passage substantially corresponds to an optical axis of the condenser, and a width of the second passage is greater than a width of the first passage so as not to impede the scattered light from entering an outmost peripheral portion of the condenser.

2. The particle measuring apparatus according to claim 1, wherein the second passage is substantially perpendicular to the first passage.

3. The particle measuring apparatus according to claim 2, wherein inner walls of the flow cell define an opening communicating said first and second passages, and said opening being sufficiently large so as not to impede the scattered light from entering the outmost peripheral portion of the condenser.

4. The particle measuring apparatus according to claim 2, wherein the second passage has a substantially rectangular cross sectional shape.

5. The particle measuring apparatus according to claim 1, wherein the second passage includes one of a pyramidal shape and a conical shape, and a central axis of the second passage substantially corresponds to that of the first passage.

6. The particle measuring apparatus according to claim 5, wherein the condenser has a condensing angle which is substantially fully utilized for condensing the light scattered by the particles.

7. The particle measuring apparatus according to claim 1, wherein the flow cell further comprises:
second passages having one of a pyramidal shape and a conical shape provided on an upstream side and a downstream side of the flow cell, respectively; and
another condenser;
wherein
central axes of the second passages substantially correspond to that of the first passage, and said condensers are provided on opposite sides of the flow cell.

8. The particle measuring apparatus according to claim 7, wherein the condenser has a condensing angle which is substantially fully utilized for condensing the light scattered by the particles.

9. The particle measuring apparatus according to claim 7, wherein the condensers are condensing lenses.

10. The particle measuring apparatus according to claim 1, wherein the condenser is a condensing lens.

11. The particle measuring apparatus according to claim 1, wherein the first passage has a substantially rectangular cross sectional shape.

12. A particle measuring apparatus comprising:
a flow cell having a first passage and a second passage extending continuously from the first passage;
a particle monitoring area formed in the first passage by irradiating the flow cell with light; and
a condenser which condenses light scattered by particles contained in sample fluid passing through the particle monitoring area so as to obtain information including diameter of the particles; wherein
a central axis of the first passage substantially corresponds to an optical axis of the condenser; and
a width of the second passage is greater than a width of the first passage so as not to impede the scattered light from entering an outmost peripheral portion of the condenser at a position where the condenser is arranged relative to the flow cell.

13. The particle measuring apparatus according to claim 12, wherein the second passage which is substantially perpendicular to the first passage and extends continuously therefrom.

14. The particle measuring apparatus according to claim 12, wherein the second passage includes one of a pyramidal shape and a conical shape and extending continuously from the first passage, and a central axis of the second passage substantially corresponds to that of the first passage.

15. The particle measuring apparatus according to claim 12, wherein the flow cell further comprises:
second passages having a pyramidal shape or a conical shape provided on an upstream side and a downstream side of the flow cell, respectively, and which extend continuously from the first passage; and
another condenser; wherein
central axes of the sub passages substantially correspond to that of the first passage, and said condensers are provided on opposite sides of the flow cell.

16. A particle measuring apparatus comprising:
a flow cell having a first passage and second passage extending continuously from the said first passage;
a particle monitoring area formed in the first passage by irradiating the flow cell with light; and
a plurality of condensers which condense light scattered by particles contained in sample fluid passing through the particle monitoring area so as to obtain information including diameter of the particles,
wherein
a central axis of the first passage substantially corresponds to an optical axis of the condensers and inner walls of the flow cell are arranged so as not to impede the scattered light from entering outmost peripheral portions of the condensers;
said condensers are provided on opposite sides of the flow cell; and
a width of the second passages is greater than a width of the first passage so as not to impede the scattered light from entering the outmost peripheral portions of the condensers.

17. The particle measuring apparatus according to claim 16, wherein the condensers are condensing lenses.

18. The particle measuring apparatus according to claim 16, wherein the second passages are disposed substantially perpendicular to the first passage.

19. The particle measuring apparatus according to claim 18, wherein the second passage extends continuously from the first passage.

20. The particle measuring apparatus according to claim 18, wherein a width of the second is greater than a width of the first passage.

* * * * *

UNITED STATES PATENT AND TRADEMARK OFFICE
CERTIFICATE OF CORRECTION

| | |
|---|---|
| PATENT NO. | : 7,170,601 B2 |
| APPLICATION NO. | : 10/528900 |
| DATED | : January 30, 2007 |
| INVENTOR(S) | : Matsuda |

It is certified that error appears in the above-identified patent and that said Letters Patent is hereby corrected as shown below:

<u>Title page</u>:
   In the title, section (54), change "FLOW CELL, AND PARTICLE MEASUREMENT DEVICE USING THE SAME" to --FLOW CELL AND PARTICLE MEASURING APPARATUS USING THE SAME--.
   After the abstract, section (57), change "20 Claims, 4 Drawing Sheets" to --18 Claims, 4 Drawing Sheets--.

<u>Column 1</u>:
   Line 1, change "FLOW CELL, AND PARTICLE" to --FLOW CELL AND PARTICLE--.
   Line 2, change "MEASUREMENT DEVICE USING THE" to --MEASURING APPARATUS USING THE--.

<u>Column 2</u>:
   Line 4, change "FIG. 3 and FIG. 4(*b*); is a modification" to --FIG. 3, and FIG. 4(*b*) is a modification--.
   Line 59, change "the outmost periphery portion" to --the outmost peripheral portion--.

<u>Column 3</u>:
   Line 58, change "achieved by combing a plurality" to --achieved by combining a plurality--.

<u>Column 4</u>:
   Line 54, change "spirit of scope" to --spirit or scope--.

UNITED STATES PATENT AND TRADEMARK OFFICE
CERTIFICATE OF CORRECTION

PATENT NO. : 7,170,601 B2
APPLICATION NO. : 10/528900
DATED : January 30, 2007
INVENTOR(S) : Matsuda It is certified that error appears in the above-identified patent and that said Letters Patent is hereby corrected as shown below:

<u>Column 6</u>:
    Line 20, change "axes of the sub passages" to --axes of the second passages--.
    Line 25, change "first passage and second passage" to --first passage and second passages--.
    Line 26, change "from the said" to --from said--.
    Lines 51-56, delete Claims 19 and 20.

Signed and Sealed this

Eighteenth Day of March, 2008

JON W. DUDAS
*Director of the United States Patent and Trademark Office*